(12) United States Patent
Cahil et al.

(10) Patent No.: US 10,227,718 B2
(45) Date of Patent: *Mar. 12, 2019

(54) MEDICAL DEVICES CONTAINING DRY SPUN NON-WOVENS OF POLY-4-HYDROXYBUTYRATE AND COPOLYMERS

(75) Inventors: Ryan Cahil, Newtonville, MA (US); Kai Guo, Brookline, MA (US); David P. Martin, Arlington, MA (US); Said Rizk, Salem, NH (US); Kicherl Ho, Groton, MA (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 1774 days.

This patent is subject to a terminal disclaimer.

(21) Appl. No.: 13/160,942

(22) Filed: Jun. 15, 2011

(65) Prior Publication Data

US 2012/0150285 A1 Jun. 14, 2012

Related U.S. Application Data

(60) Provisional application No. 61/354,994, filed on Jun. 15, 2010.

(51) Int. Cl.
*D04H 1/42* (2012.01)
*A61L 27/18* (2006.01)
(Continued)

(52) U.S. Cl.
CPC ............... *D04H 1/42* (2013.01); *A61L 27/18* (2013.01); *A61L 27/54* (2013.01); *A61L 29/06* (2013.01);
(Continued)

(58) Field of Classification Search
USPC .................................. 424/1.11, 91; 442/334
See application file for complete search history.

(56) References Cited

U.S. PATENT DOCUMENTS

| 5,811,272 A | 9/1998 | Snell |
| 6,245,537 B1 | 6/2001 | Williams |

(Continued)

FOREIGN PATENT DOCUMENTS

| EP | 0628586 | 12/1994 |
| EP | 2505213 | 10/2012 |

(Continued)

OTHER PUBLICATIONS

Duvernoy, et al. "A biodegradable patch used as a pericardial substitute after cardiac surgery: 6- and 24-month evaluation with CT", Thorac. Cardiovacs. Surgeon, 43:271-274 (1995).
(Continued)

*Primary Examiner* — Lynda Salvatore
(74) *Attorney, Agent, or Firm* — Pabst Patent Group LLP

(57) ABSTRACT

Continuous processing methods for making absorbable polymeric dry spun non-wovens with one or more of the following properties: high burst strength, fine fibers of average diameter from 0.01 μm to 50 μm, and thickness from 10 μm to 10 mm, have been developed. Improved fiber cohesion is made possible by controlling the tackiness of the fibers of the non-woven during web collection. The polymer is preferably a polyhydroxyalkanoate, more preferably, a 4-hydroxybutyrate polymer or copolymer. A non-woven of poly-4-hydroxybutyrate is most preferred. The non-wovens have fine fibers with average diameters ranging from 0.01 μm to 50 μm, and are derived by dry spun processing, during which a solution of polymer(s) is injected into a stream of high velocity air with a pressure of 1 to 500 psi for solvent stripping and polymer strand attenuation. The non-wovens can be used for a variety of purposes including fabrication of medical devices.

15 Claims, 1 Drawing Sheet

(51) Int. Cl.
  A61L 27/54    (2006.01)
  A61L 29/06    (2006.01)
  A61L 29/16    (2006.01)
  A61L 31/06    (2006.01)
  A61L 31/16    (2006.01)
  D04H 1/56     (2006.01)
  D04H 3/16     (2006.01)

(52) U.S. Cl.
  CPC .............. *A61L 29/16* (2013.01); *A61L 31/06* (2013.01); *A61L 31/16* (2013.01); *D04H 1/56* (2013.01); *D04H 3/16* (2013.01); *A61L 2300/00* (2013.01); *Y10T 442/608* (2015.04)

(56) References Cited

U.S. PATENT DOCUMENTS

| | | |
|---|---|---|
| 6,316,262 B1 | 11/2001 | Huisman |
| 6,323,010 B1 | 11/2001 | Skraly |
| 6,548,569 B1 | 4/2003 | Williams |
| 6,555,123 B2 | 4/2003 | Williams |
| 6,585,994 B2 | 7/2003 | Williams |
| 6,610,764 B1 | 8/2003 | Martin |
| 6,623,748 B2 | 9/2003 | Clokie |
| 6,828,357 B1 | 12/2004 | Martin |
| 6,838,493 B2 | 1/2005 | Williams |
| 6,867,247 B2 | 3/2005 | Williams |
| 6,867,248 B1 | 3/2005 | Martin |
| 6,878,758 B2 | 4/2005 | Martin et al. |
| 6,905,987 B2 | 6/2005 | Noda |
| 7,025,980 B1 | 4/2006 | Williams |
| 7,179,883 B2 | 2/2007 | Williams |
| 7,244,442 B2 | 7/2007 | Williams |
| 7,268,205 B2 | 9/2007 | Williams |
| 8,287,909 B2* | 10/2012 | Martin et al. ............... 424/489 |
| 8,431,060 B2* | 4/2013 | Huang et al. ............... 264/310 |
| 2003/0211131 A1 | 11/2003 | Martin |
| 2005/0158542 A1 | 7/2005 | Iwata |
| 2009/0012604 A1 | 1/2009 | Schmitz |
| 2009/0162276 A1* | 6/2009 | Martin .................. A61L 15/26 424/1.11 |
| 2011/0236974 A1 | 9/2011 | Ogle |
| 2014/0277572 A1* | 9/2014 | Martin et al. ............ 623/23.58 |

FOREIGN PATENT DOCUMENTS

| | | |
|---|---|---|
| WO | 9523249 | 8/1995 |
| WO | 9932536 | 7/1999 |
| WO | 0056376 | 9/2000 |
| WO | 2004101002 | 11/2004 |
| WO | 2006015276 | 2/2006 |
| WO | 2007092464 | 8/2007 |
| WO | 2009085823 | 7/2009 |
| WO | 2011106205 | 9/2011 |

OTHER PUBLICATIONS

Hori, et al., "Chemical synthesis of high molecular weight poly(3-hydroxybutyrate-co-4-hydroxybutyrate)", Polymer 36:4703-4705 (1995).

Houk, et al., "Why delta-valerolactone polymerizes and gamma-butyrolactone does not", J. Org. Chem., 73 (7), 2674-2678 (2008).

Martin and Williams, "Medical Applications of Poly-4-hydroxybutyrate: A Strong Flexible Absorbable Biomaterial", Biochem. Eng. J., 16:97-105 (2003).

Steinbüchel, et al., "Diversity of Bacterial Polyhydroxyalkanoic Acids", FEMS Microbial. Lett., 128:219-228 (1995).

Williams, et al., "Applications of PHAs in Medicine and Pharmacy, in Biopolymers", Polyesters, III, 4:91-127 (2002).

* cited by examiner

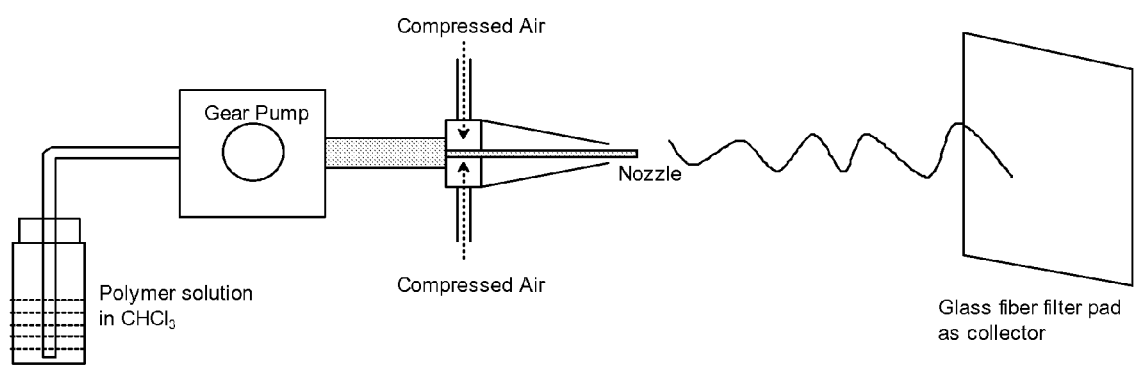

MEDICAL DEVICES CONTAINING DRY SPUN NON-WOVENS OF POLY-4-HYDROXYBUTYRATE AND COPOLYMERS

CROSS-REFERENCE TO RELATED APPLICATIONS

This application claims the benefit of priority to U.S. Ser. No. 61/354,994, filed on Jun. 15, 2010.

FIELD OF THE INVENTION

The present invention generally relates to polymeric compositions that can be processed into dry spun non-wovens using continuous processes. The compositions include polymers or copolymers comprising 4-hydroxybutyrate, and can be processed into non-wovens that have high burst strength, and retain polymer molecular weight.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, Tepha-FLEX® biomaterial) is a strong, pliable thermoplastic polyester that, despite its biosynthetic route, has a relatively simple structure.

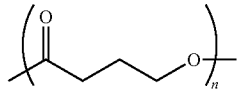

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production. Several biosynthetic routes are currently known to produce P4HB:

This schematic shows some of the known biosynthetic pathways for the production of P4HB. Pathway enzymes are: 1. Succinic semialdehyde dehydrogenase, 2. 4-hydroxybutyrate dehydrogenase, 3. diol oxidoreductase, 4. aldehyde dehydrogenase, 5. Coenzyme A transferase and 6. PHA synthetase.

Chemical synthesis of P4HB has been attempted, but it has been impossible to produce the polymer with a sufficiently high molecular weight that is necessary for most applications (see Hori, Y., et al., *Polymer* 36:4703-4705 (1995) and Houk, et al., *J. Org. Chem.*, 73(7):2674-2678 (2008).

U.S. Pat. Nos. 6,245,537, 6,623,748 and 7,244,442 describe methods of making PHAs with little to no endotoxin, which is suitable for medical applications. U.S. Pat. Nos. 6,548,569, 6,838,493, 6,867,247, 7,268,205, and 7,179,883 describe use of PHAs to make medical devices. Copolymers of P4HB include 4-hydroxybutyrate copolymerized with 3-hydroxybutyrate or glycolic acid (U.S. patent application No. 2003/0211131 by Martin and Skraly, U.S. Pat. No. 6,316,262 to Huisman et al., and U.S. Pat. No. 6,323,010 to Skraly, et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams, et al. and WO 99/32536 to Martin, et al. Applications of P4HB have been reviewed in Williams, et al., *Polyesters, III*, 4:91-127 (2002), and by Martin, et al. "Medical Applications of Poly-4-hydroxybutyrate: A Strong Flexible Absorbable Biomaterial", *Biochem. Eng. J.* 16:97-105 (2003). Medical devices and applications of P4HB have also been disclosed by WO 00/56376 to Williams, et al. Several patents including U.S. Pat. Nos. 6,555,123, 6,585,994, and 7,025,980 describe the use of PHAs in tissue repair and engineering.

In the practice of surgery there currently exists a need for absorbable non-wovens with improved performance. These non-wovens can be used, for example, for soft tissue repair, to reinforce tissue structures, to separate tissues, and to serve as tissue engineering scaffolds, including guided tissue regeneration scaffolds. They may also be used as components of other devices. A number of other absorbable materials have been used to produce non-wovens for use in surgery. For example, non-wovens have been made from

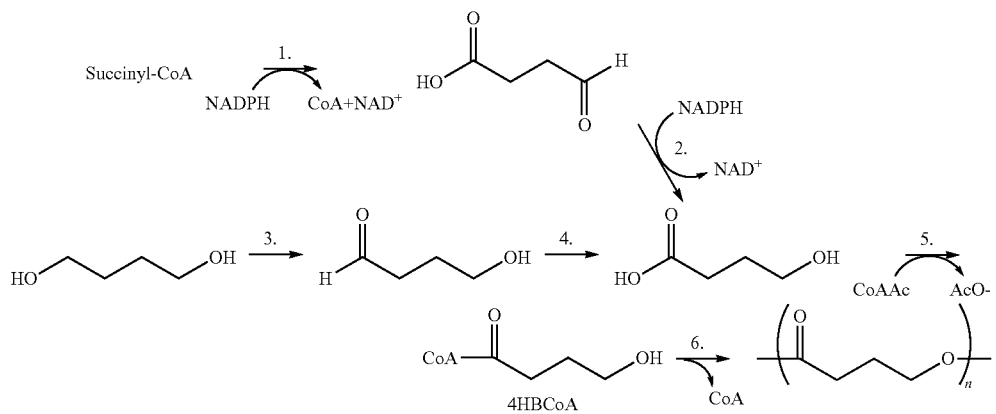

polyglycolic acid (PGA) or copolymers containing lactic acid. These materials do not, however, have ideal properties for many procedures and applications. Non-wovens made from polyglycolic acid breakdown too rapidly for many applications, and release acidic degradation products that can cause inflammatory reactions.

WO 04/101002 to Martin et al. discloses monofilament and multifilament knitted meshes of P4HB, produced by knitting monofilament and multifilament fibers of P4HB. WO 09/085,823 to Ho, et al. discloses medical devices containing melt-blown non-wovens of poly-4-hydroxybutyrate and copolymers thereof. Notably, the process of melt blowing can limit the utility of this method to produce non-wovens, particularly when it is necessary to produce three-dimensional non-woven fabrics and devices, and apply coatings of non-wovens on scaffolds or other materials. The process of melt extrusion causes a dramatic loss in the molecular weight of the polymer such that the molecular weight of the polymer in the melt blown non-woven is substantially less than in the polymer feed. The lower molecular weight of melt blown non-woven is a particular disadvantage when it is desirable to retain mass and/or mechanical properties, such as burst strength, in vivo, for a prolonged period of time, since lower molecular weight P4HB non-wovens degrade faster in vivo than higher molecular weight P4HB non-wovens.

WO 95/23249 to Noda, et al. discloses non-woven fabrics prepared from other polyhydroxyalkanoates, namely, poly-3-hydroxybutyrate (PHB) and poly-3-hydroxybutyrate-co-3-hydroxyvalerate (PHBV), by dry spinning for use in non-medical applications such as disposable absorbent articles, including diapers, incontinence articles, and sanitary napkins. These materials, however, have substantially different thermal and physical properties than poly-4-hydroxybutyrate and copolymers thereof. For example, P3HB has a melting point and glass transition temperature of approx. 180° C. and 1° C., respectively, and an elongation to break of about 3%, whereas P4HB has a melting point of 60° C., a glass transition temperature of approx. −51° C., and elongation to break of around 1,000%. As such, P3HB is a brittle polymer that has properties resembling polystyrene whereas P4HB is a strong but extensible polymer similar to low density polypropylene. Furthermore, P3HB and PHBV have also been reported to degrade very slowly in vivo, with material still present after 24 months (Duvernoy, et al. *Thorac. Cardiovacs. Surgeon,* 43:271-274 (1995)), and are therefore not well suited for many in vivo surgical applications.

It is an object of the present invention to provide methods to produce dry spun non-wovens of absorbable P4HB and copolymers thereof that have relatively high burst strengths, and without substantial loss of the polymer molecular weight during processing.

It is a further object of the present invention to provide continuous processes to produce medical devices comprising non-wovens by dry spinning, including processes to form medical devices by coating other materials and scaffolds with dry spun non-wovens, and processes to dry spin P4HB and copolymers thereof into non-wovens without substantial loss of molecular weight during the spinning process.

It is another object of the present invention to provide dry spun non-wovens which are biocompatible and can be used in medical applications, for example, as implants such as devices for soft tissue repair, replacement, and regeneration, temporary tissue support, tissue separation, as well as devices or components of devices for tissue in-growth (or guided tissue regeneration) and tissue engineering.

It is therefore an object of the invention to provide continuous processes for dry spun non-woven production, which can be incorporated into or formed into medical devices with excellent physical and mechanical properties for medical applications.

SUMMARY OF THE INVENTION

Continuous processing methods for making absorbable polymeric non-wovens, without substantial loss of polymer molecular weight during processing, with one or more of the following properties: burst strength greater than 0.001 Kgf, high toughness, low modulus, high molecular weight, and thickness from 10 µm to 10 mm, have been developed. The non-wovens have unexpectedly good cohesion of the fibers in the non-wovens due to fusion of the fibers, which remain tacky, during the web collection process. In the preferred embodiment, the polymer is a polyhydroxyalkanoate, and in the most preferred embodiment, the polymer comprises 4-hydroxybutyrate. A particularly preferred embodiment is a non-woven of poly-4-hydroxybutyrate or copolymer thereof, wherein the non-woven comprises fine fibers with average diameters ranging from 0.01 µm to 50 µm, wherein the non-woven is derived by dry spun processing, and wherein a solution of the polymer is injected into a stream of high velocity gas with a pressure of 1 to 500 psi for solvent stripping and polymer strand attenuation. These can be used for a variety of purposes including fabrication of medical devices.

BRIEF DESCRIPTION OF THE DRAWINGS

FIG. 1 is a diagram of the process to manufacture dry spun non-woven materials from poly-4-hydroxybutyrate and copolymers thereof.

DETAILED DESCRIPTION OF THE INVENTION

Definitions

"Poly-4-hydroxybutyrates", as generally used herein, means a homopolymer comprising 4-hydroxybutyrate units. It may be referred to herein as P4HB or TEPHAFLEX® biomaterial (manufactured by Tepha, Inc., Lexington, Mass.).

"Copolymers of poly-4-hydroxybutyrate", as generally used herein, means any polymer comprising 4-hydroxybutyrate with one or more different hydroxy acid units.

"Bicomponent", as generally used herein, means a non-woven comprising two thermoplastic materials.

"Blend", as generally used herein, means a physical combination of different polymers, as opposed to a copolymer comprised of two or more different monomers.

"Burst strength", as used herein, is determined by test method ASTM D6797-02 "Standard test method for bursting strength of fabrics constant rate of extension (CRE) ball burst test," using a MTS Q-Test Elite universal testing machine, or similar device. The testing fixture uses a one-inch diameter ball and a 1.75-inch diameter circular opening. Non-woven samples are tested with a pre-load setting of 0.05 Kg, and a ball rate of 305 mm/minute until failure.

"Tensile modulus" is the ratio of stress to strain for a given material within its proportional limit.

"Toughness" means a property of a material by virtue of which it can absorb energy; the actual work per unit volume or unit mass of material that is required to rupture it. Toughness is usually proportional to the area under the load-elongation curve such as the tensile stress-strain curve. (Rosato's Plastics Encyclopedia and Dictionary, Oxford Univ. Press, 1993)

"Elongation" or extensibility of a material, means the amount of increase in length resulting from, as an example, the tension to break a specimen. It is expressed usually as a percentage of the original length. (Rosato's Plastics Encyclopedia and Dictionary, Oxford Univ. Press, 1993)

"Molecular weight", as used herein, unless otherwise specified, refers to the weight average molecular weight (Mw), not the number average molecular weight (Mn), and is measured by GPC relative to polystyrene.

"Absorbable" as generally used herein means the material is broken down in the body and eventually eliminated from the body within five years.

"Biocompatible" as generally used herein means the biological response to the material or device being appropriate for the device's intended application in vivo. Any metabolites of these materials should also be biocompatible.

I. Composition

Methods have been developed to produce medical devices comprising non-wovens of P4HB and copolymers thereof with high burst strength. These methods may be used to prepare non-wovens with fine fibers ranging in average diameter from 0.01 µm to 50 µm. A major advantage of the method over melt blown processing is that the molecular weight of the polymer may decrease less than 20% of its original value during dry spun processing.

A. Polymers

The processes described herein can typically be used with poly-4-hydroxybutyrate (P4HB) or a copolymer thereof. Copolymers include P4HB with another hydroxyacid, such as 3-hydroxybutyrate, and P4HB with glycolic acid or lactic acid monomer. P4HB and copolymers thereof can be obtained from Tepha, Inc. of Lexington, Mass.

In a preferred embodiment, the P4HB homopolymer and copolymers thereof have a molecular weight, Mw, within the range of 50 kDa to 1,200 kDa (by GPC relative to polystyrene) and more preferably from 100 kDa to 600 kDa.

If desired, the PHA polymers may be blended or mixed with other materials prior to dry spinning. In a particularly preferred embodiment, P4HB and its copolymers may be blended with other absorbable polymers. Examples of other absorbable polymers include, but are not limited to, polymers comprising glycolic acid, lactic acid, 1,4-dioxanone, trimethylene carbonate, 3-hydroxybutyric acid, and caprolactone, including polyglycolic acid, polylactic acid, polydioxanone, polycaprolactone, copolymers of glycolic and lactic acids, polyglycolic acid:trimethylene carbonate polymers, and copolymers of glycolide and ε-caprolactone. The ratio of the PHA polymer in the blend to the non-PHA polymer component(s) may be varied in order to select the desired properties of the dry spun non-woven.

B. Non-Wovens

In a preferred embodiment, non-wovens can be prepared with a thickness of less than 10 mm, but greater than 10 µm. More preferably the thickness is between 50 µm and 3 mm. It has been discovered that non-wovens of P4HB polymer or copolymers thereof can be prepared by dry spinning with unexpectedly high retention of polymer molecular weight, and high burst strengths. Notably, the molecular weight of the polymer decreases less than 20% during dry spinning. In a preferred embodiment, the poly-4-hydroxybutyrate or copolymer has a weight average molecular weight greater than 50 kDa relative to polystyrene. In a more preferred embodiment, the non-woven of claim 1 wherein the poly-4-hydroxybutyrate or copolymer has a weight average molecular weight greater than 210 kDa relative to polystyrene.

In contrast, non-wovens of P4HB or copolymers thereof prepared by melt blowing typically lose a significant amount of the polymer's initial molecular weight during melt processing. This results in a non-woven with significantly reduced molecular weight. WO 09/085,823 to Ho, et al., for example, describes methods to produce non-wovens of P4HB and copolymers thereof by melt processing wherein the polymer loses up to 50% of the polymer's initial molecular weight.

The non-wovens produced according to the methods described herein have high burst strengths and improved fusion of the fibers at their crossover points. Burst strengths exceed 0.001 Kgf, and more preferably exceed 0.01 Kgf. For example, a dry spun non-woven of P4HB with an areal density of 13.3 g/m$^2$ has a burst strength of 0.75 Kgf. In comparison, a melt blown non-woven produced by the method of WO 09/085,823 to Ho et al., with an areal density that is 2.9 times higher, namely 38.5 g/m$^2$, has a burst strength that is only about 2 times higher (i.e. 1.55 Kgf).

Burst strength of the non-wovens can be determined by ASTM D6797-02, Standard Test Method for Bursting Strength of Fabrics Constant-Rate-of-Extension (CRE) Ball Burst Test. The testing fixture comprises a 1-inch diameter ball, and a fixture with a 1.75-inch diameter circular opening. The non-woven samples are tested using a universal testing machine, for example, a Q-Test Elite by MTS, with a pre-load setting of 0.05 Kg, and a ball rate set at 305 mm/minute until failure. The ball is pushed through the sample at a constant rate and force over extension curve is recorded. Breaking load (Kgf), elongation at break (mm) and location of break are recorded.

C. Other Components

The P4HB polymer and copolymer dry spun non-wovens may contain other materials, including plasticizers, nucleants, other polymers, additives, dyes, and compatibilizers. Examples of plasticizers are disclosed by U.S. Pat. No. 6,905,987 to Noda et al. Other components may be added to impart benefits such as, but not limited to, increased stability, including oxidative stability, brightness, color, flexibility, resiliency, workability, processability (by addition of processing aids), and viscosity modifiers.

In addition to adding other components directly to the P4HB polymer or copolymer thereof, it is also possible to prepare bicomponent non-wovens of P4HB or its copolymers. These bicomponent non-wovens can be prepared by dry spinning at least two polymers simultaneously, either from the same solution or from separate spinning nozzles. Additionally, layered structures may be created by first spinning one type of polymer (or mixture) and then spinning another, or spinning from different directions.

Active components, including therapeutic, diagnostic and/or prophylactic agents, or other substances may be incorporated into the non-wovens, either at the time of dry spinning, or in a later processing step. Such compositions may be used for controlled release of the drugs or other substances. These may be proteins, peptides, sugars, polysaccharides, glycoproteins, lipids, lipoproteins, nucleic acid molecules, inorganic or organic synthetic molecules, or combinations thereof. The non-wovens may comprise cells, proteins, or other substances including allograft and xenograft materials. It may be advantageous to incorporate contrast agents, radiopaque markers, or radioactive substances.

For certain applications it may also be desirable to incorporate fillers, including materials such as titanium dioxide, calcium carbonate, hydroxyapatite, and tricalcium phosphate.

D. Formation into Devices

Non-wovens made from P4HB polymers and copolymers thereof by dry spun processes are characterized by their formation from fine fibers with average diameters ranging from 0.01 μm to 50 μm. Notably, the dry spun non-wovens may be produced with smaller fibers than the melt-blown non-wovens. The dry spun non-wovens are also characterized by their high burst strengths, exceeding 0.001 Kgf, and molecular weights within 20% of the value of the polymer from which they are derived. These non-wovens have properties that are substantially improved for many medical applications relative to PGA-based non-wovens. Because these dry spun non-wovens can be produced without substantial loss of molecular weight, they can also have significant advantages over melt-blown non-wovens. This is of particular significance where it is desirable for a non-woven material to retain its integrity and strength in vivo for a longer period of time. For example, in tissue engineering it may be desirable for a non-woven scaffold to be present in vivo for a prolonged period of time to allow tissue in-growth and tissue maturation before the scaffold is absorbed. Premature absorption of the scaffold will result in immature tissue formation, and potentially failure of the implant device. Thus, because dry spun non-wovens can be prepared without substantial loss of polymer molecular weight, and the body requires longer periods of time to degrade P4HB and copolymers thereof of higher molecular weight, a dry spun non-woven will remain in vivo as a scaffold for longer than a melt blow non-woven.

The non-wovens possess properties that are desirable in preparing medical products, particularly implantable medical devices. For example, the non-wovens may be used to make partially or fully absorbable biocompatible medical devices, or components thereof. Such devices include, but are not limited to, stent, stent graft, stent coating, drug delivery device, device for temporary wound or tissue support, device for soft tissue repair or regeneration, repair patch, tissue engineering scaffolds, retention membranes (for example, to retain bone graft), anti-adhesion membrane, tissue separation membrane, hernia repair device, device coating (including devices to improve fixation), cardiovascular patch, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, including, but not limited to, atrial septal defect repair devices and patent foramen ovale (PFO) closure devices, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

II. Methods of Manufacturing Non-Wovens

Methods have been developed to produce medical devices comprising non-wovens of P4HB and copolymers thereof with high burst strength. These methods may be used to prepare non-wovens with fine fibers ranging in average diameter from 0.01 μm to 50 μm. The methods may be run continuously, which is particularly advantageous in manufacturing. These non-wovens are prepared by dry spinning A major advantage of the method over melt blown processing is that the molecular weight of the polymer may decrease less than 20% of its original value during dry spun processing. Due to the low processing temperature, the dry spinning approach can have other advantages over melt spinning, particularly in cases where the spinning mixture contains thermally sensitive materials, such as drugs, polymer or other additive. In these cases it may be possible to reduce thermal degradation by using dry spinning rather than melt spinning.

In addition to retaining polymer molecular weight, non-wovens with high burst strength can produced by controlling the formation of the web. Tackiness of the fibers collected at the web can be controlled to improve fusion of the fibers at their crossover points. Unexpectedly high cohesion of the fibers within the dry spun non-woven can be achieved by controlling the stripping rate of the solvent and the tackiness of the fibers during the web collection process leading to improved fusion of the fibers at their crossover points.

With appropriate choice of solution flow rate (ml/min), distance between the nozzle and the collector, needle diameter, needle extrusion distance, temperature, choice of solvent, collection time, polymer molecular weight, and gas (e.g. air) pressure, high burst strength non-wovens comprising fine fibers with average diameters of 0.01 μm to 50 μm can be prepared. For example, dry spun non-wovens of P4HB with a thickness of 0.097 mm can be prepared with a burst strength of 0.47 Kgf. Increasing the thickness to 0.106 mm can increase the burst strength to 0.75 Kgf.

A. Method of Making P4HB Polymer or Copolymer Non-Wovens by Dry Spinning

In a preferred method, a non-woven of P4HB polymer or copolymer may be prepared as follows. The P4HB polymer is dissolved in a solvent to make a polymer solution. A suitable dry spinning apparatus is shown in FIG. 1. This consists of a nozzle through which the polymer solution is injected into a stream of accelerated gas. A preferred set up comprises compressed air as the source of gas (controlled by a pressure regulator), a REGLO-Z digital pump drive equipped with a suction shoe pump head to control the injection rate of the polymer solution, a spraying apparatus that consists of concentric nozzles, and a fiber glass pad as the collector. The collector is positioned at a desired fixed distance from the nozzle. The spraying apparatus consists of an inner and a concentric outer nozzle, which creates a low pressure region near the orifice of the inner nozzle. Polymer strands are consistently shot to the fiber glass pad collector due to the combination of the low pressure zone and stripping at the solution/gas interface. Solvent evaporates during the time the polymer strand hits the collector due to the high surface to volume ratio of the strands coupled with the high gas turbulence and temperature.

A number of parameters can be varied to control the non-woven thickness, density and fiber sizes including, but not limited to, solution flow rate (ml/min), distance between the nozzle and the collector, needle configuration (including needle diameter and needle extrusion distance), temperature, choice of solvent, polymer molecular weight, collection time, and gas (e.g. air) pressure.

B. Method of Making Three-Dimensional P4HB Polymer or Copolymer Non-Wovens by Dry Spinning A particular advantage of the dry spun method described herein over melt blown methods is that non-woven can be spun directly onto scaffolding structures to make three dimensional structures. This is achieved by either positioning the scaffold at the fiber collection plate and rotating the scaffolding structure during fiber collection, or alternatively, rotating the nozzle around the scaffold.

The present invention will be further understood by referenced to the following non-limiting example.

Example 1

Preparation of P4HB Non-Woven by Dry Spinning

P4HB (Tepha, Inc., Lexington, Mass.) (M, 490 kDa) was dissolved in chloroform to make an 8% (wt/vol) polymer solution. P4HB dry spun non-woven was produced as described in method IIA above using the following conditions:
Solution flow rate: 3 mL/min
Distance between nozzle and collector: 32 inches
Needle: 0.035" ID×0.375" extrusion distance
Air pressure: 55 psi
Temperature: Ambient
Collection time: 6 minutes The molecular weight $M_w$ of the dry spun non-woven was determined by GPC relative to polystyrene, and found to be 474 kDa. Therefore the P4HB polymer lost a $M_w$ of only 16 kDa (or approx. 3%) during processing into the dry spun non-woven.

Using methods similar to that described above the following dry spun non-wovens was prepared:

| Reference | Areal Density (g/m$^2$) | Burst Strength (Kgf) |
|---|---|---|
| KG02-105-4 | 13.3 | 0.75 |

Example 2

Preparation of a P4HB Non-Woven/Chitosan Patch by Dry Spinning

A similar procedure to that described in Example 1 was used to dry spin a P4HB non-woven directly onto a chitosan patch, except that the chitosan patch was placed in the collector position and the distance between the patch and the nozzle was adjusted to 30 inches. Collection times of 1, 2, 4, 6 and 8 minutes were used to make samples.

Example 3

Comparison of Dry Spun and Melt Blown Non-Woven Molecular Weights

Several samples of P4HB melt-blown non-woven were prepared according to the procedure of Example 1 of WO 09/085,823 to Ho et al. using P4HB with a starting molecular weight ($M_w$) of 328 kDa. The molecular weight (Mw) of the resulting P4HB melt-blown non-wovens was found to be 207 to 157 kDa, representing a 47 to 52% decrease in the molecular weight ($M_w$) of the polymer during processing. This compares to a molecular weight ($M_w$) decrease of just 3% for the dry spun P4HB non-woven produced in Example 1. Thus it is apparent that for any given P4HB polymer resin, production of a non-woven by dry spinning will yield a much higher molecular weight fabric than by melt blowing.

Example 4

Preparation of Poly-4-hydroxybutyrate-co-3-hydroxybutyrate Copolymer (PHA3444) Non-Woven by Dry Spinning PHA3444 (Sample ID: DM23.61A, Tepha, Inc., Lexington, Mass.) (M, 651 kDa, 24% 4-hydroxybutyrate co-monomer) was dissolved in chloroform to make a 12% (wt/vol) polymer solution. PHA3444 dry spun non-woven was produced as described in method IIA above using the following conditions:
Solution flow rate: 32 mL/min
Distance between nozzle and collector: 30 inches
Needle: 0.035" ID×0.375" extrusion distance
Air pressure: 20 psi
Temperature: Ambient
Collection time: 5 minutes Modifications and variations of the methods and compositions will be apparent from the foregoing detailed description and are intended to come within the scope of the appended claims.

We claim:
1. A non-woven comprising poly-4-hydroxybutyrate (P4HB) or copolymer thereof, wherein the non-woven comprises fine fibers having an average diameter of from about 0.01 µm to about 50 µm, and a burst strength greater than 0.001 Kgf, wherein the non-woven is prepared by dry spinning P4HB or a copolymer thereof under conditions decreasing the initial weight average molecular weight of the P4HB or copolymer thereof less than 20% and wherein when the non-woven has an areal density of about 13.3 g/m$^3$, the non-woven has a burst of strength of about 0.75 Kgf as determined by the ASTM D6797-02 Standard Test Method for Burst Strength.

2. The non-woven of claim 1 wherein the weight average molecular weight of the P4HB or copolymer thereof decreases less than 20% during the processing of the polymer or copolymer into the dry spun non-woven.

3. The non-woven of claim 1 wherein the P4HB or copolymer thereof has a weight average molecular weight greater than 50 kDa relative to polystyrene.

4. The non-woven of claim 1 wherein the P4HB or copolymer thereof has a weight average molecular weight greater than 210 kDa relative to polystyrene.

5. The non-woven of claim 1 wherein the P4HB or copolymer thereof is dissolved in a volatile solvent, and injected into a stream of accelerated gas at 1 to 500 psi (6.9 to 3,447 kPa) to form polymer strands, and the polymer strands are attenuated by the high velocity gas.

6. The non-woven of claim 1 formed into a device.

7. The device of claim 6 wherein the device is used for the repair, regeneration or replacement of soft tissue.

8. The device of claim 6 selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, atrial septal defect repair device, PFO (patent foramen ovale) closure device, left atrial appendage (LAA) closure device, pericardial patch, bulking agent, filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

9. The non-woven of claim 1 further comprising a second polymer selected from the group consisting of a polymer of glycolic acid, lactic acid, 1,4-dioxanone, trimethylene carbonate, caprolactone and combinations thereof.

10. The non-woven of claim 1 further comprising additives selected from the group consisting of prophylactic agents; diagnostic agents; therapeutic agents; other polymers; proteins; growth factors; plasticizers; nucleants; compatibilizers; porogens; radiolabelled substances; imaging agents; radiopaque markers; contrast agents; anti-oxidants; dyes; viscosity modifiers; and odor control agents.

11. The device of claim 6, wherein the non-woven is dry spun from the liquid resin mixture directly onto a scaffold or other substrate to form the device.

12. A method of using a device formed of a non-woven of P4HB or copolymer thereof, wherein the non-woven comprises fine fibers having an average diameter of from about 0.01 µm to about 50 µm, and a burst strength greater than 0.001 Kgf, wherein the non-woven is prepared by dry spinning of the polymer under conditions decreasing the initial weight average molecular weight of the P4HB or copolymer thereof less than 20%, and the extruded polymer strands are attenuated by high velocity air to form the non-woven and wherein when the non-woven has an areal density of about 13.3 g/m$^3$, the non-woven has a burst of strength of about 0.75 Kgf as determined by the ASTM D6797-02 Standard Test Method for Burst Strength,
comprising inserting or implanting the device into an individual in need thereof.

13. The method of claim 12 wherein the device is selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

14. The method of claim 12 wherein the fibers initially remain tacky during web collection, and subsequently fuse at their crossover points.

15. A method of making a medical device comprising dry spun non-woven of P4HB or copolymer thereof,
wherein the non-woven comprises fine fibers having an average diameter of from about 0.01 µm to about 50 µm, and a burst strength greater than 0.001 Kgf, wherein the non-woven is prepared by dry spinning P4HB or a copolymer thereof under conditions decreasing the initial weight average molecular weight of the P4HB or copolymer thereof less than 20% and wherein when the non-woven has an areal density of about 13.3 g/m$^3$, the non-woven has a burst of strength of about 0.75 Kgf as determined by the ASTM D6797-02 Standard Test Method for Burst Strength, the method comprising forming the non-woven into the device.

* * * * *